US012685289B2

(12) United States Patent
Mery et al.

(10) Patent No.: US 12,685,289 B2
(45) Date of Patent: Jul. 21, 2026

(54) CONCENTRATED ALGAL EXTRACT

(71) Applicants: UPL Corporation Limited, Port Louis (MU); UPL Europe LTD, Warrington (GB)

(72) Inventors: Aude Bernardon Mery, Port Louis (MU); Arnaud LaBarre, Warrington (GB); Elisabeth Douce, Warrington (GB); Gregory LeCollinet, Warrington (GB); Sheldon Park, Warrington (GB); Céline Conan, Warrington (GB); Anne Guiboileau, Warrington (GB); Paul Yohan, Warrington (GB); Samantha Besse, Warrington (GB)

(73) Assignees: UPL CORPORATION LIMITED, Port Louis (MU); UPL EUROPE LTD., Cheshire (GB)

( * ) Notice: Subject to any disclaimer, the term of this patent is extended or adjusted under 35 U.S.C. 154(b) by 856 days.

(21) Appl. No.: 17/767,101

(22) PCT Filed: Sep. 30, 2020

(86) PCT No.: PCT/GB2020/052369
§ 371 (c)(1),
(2) Date: Apr. 7, 2022

(87) PCT Pub. No.: WO2021/069866
PCT Pub. Date: Apr. 15, 2021

(65) Prior Publication Data
US 2022/0361435 A1 Nov. 17, 2022

(30) Foreign Application Priority Data
Oct. 7, 2019 (EP) .................................... 19306297

(51) Int. Cl.
*A01H 13/00* (2006.01)
*A01N 65/03* (2009.01)
*C05G 5/27* (2020.01)

(52) U.S. Cl.
CPC ............. *A01H 13/00* (2013.01); *A01N 65/03* (2013.01)

(58) Field of Classification Search
CPC ........ A01H 13/00; A01N 65/03; A01N 65/00; A01N 61/00; C05G 5/27; C05G 3/00; C05F 11/00; A01P 21/00
See application file for complete search history.

(56) References Cited

U.S. PATENT DOCUMENTS

| | | | |
|---|---|---|---|
| 4,897,266 A | 1/1990 | Herve et al. | |
| 5,508,033 A | 4/1996 | Briand | |
| 6,312,709 B1 | 11/2001 | Allen et al. | |
| 6,346,252 B1 | 2/2002 | Moigne | |
| 6,841,572 B2 * | 1/2005 | Horst ...................... | A01N 37/36 514/568 |
| 8,815,570 B2 | 8/2014 | Weber et al. | |
| 9,854,810 B2 | 1/2018 | Meeder | |
| 2004/0011101 A1 * | 1/2004 | Newton ................. | A01N 65/03 71/23 |
| 2005/0048080 A1 | 3/2005 | Katzen | |
| 2011/0020881 A1 | 1/2011 | Cho et al. | |
| 2011/0142875 A1 | 6/2011 | Piccirilli | |
| 2012/0302742 A1 | 11/2012 | Hjelland et al. | |
| 2015/0351408 A1 | 12/2015 | Meeder | |
| 2017/0251677 A1 | 9/2017 | Hery | |
| 2022/0015374 A1 | 1/2022 | Hery | |
| 2022/0015375 A1 | 1/2022 | Hery | |
| 2022/0015376 A1 | 1/2022 | Hery | |

FOREIGN PATENT DOCUMENTS

| | | |
|---|---|---|
| CN | 1669441 A | 9/2005 |
| CN | 102131916 A | 7/2011 |
| EP | 0538091 A1 | 1/1996 |
| ES | 2150275 T3 | 11/2000 |
| JP | 2008120707 A | 5/2008 |
| KR | 100984217 B1 | 9/2010 |
| RU | 2308203 C1 | 10/2007 |
| WO | 8402652 A1 | 7/1984 |
| WO | 9107946 A1 | 6/1991 |
| WO | 0209513 A2 | 2/2002 |
| WO | 2013120729 A1 | 8/2013 |
| WO | 2015011411 A1 | 1/2015 |

OTHER PUBLICATIONS

Craigie JS. Seaweed extract stimuli in plant science and agriculture. J Appl Phycol. 2011;23:371-393.*
Nieber et al. Maintenance for Infiltration Practices. Maintenance for Infiltration Practices | Stormwater Treatment: Assessment and Maintenance. 2019;1-3.*
James DE. Culturing algae. Carolina Biological Supply Co. 1978; 1-28.*
Taulbee et al. Centrifugation|Preparative. In Encyclopedia of Analytical Science, 2nd ed.; Elsevier: Amsterdam, The Netherlands, 2005;469-481.*
Anonymous; "Acadian 100% Soluble Seaweed Extract Powder" [Product Sheet]; Organic Crop Protectants Pty LTD; retrieved on Aug. 11, 2022 from "https://ocp.com.au/wp-content/uploads/2021/03/Acadian-Seaweed-Powder-Flyer-1.pdf"; 2 pages.
Anonymous; "Algifert-K-Powder" [Product Info]; Humos Manufacturing LTD; May 1, 2018; Retrieved on Apr. 13, 2023 from "https://www.humefert.com/wp-content/uploads/2018/05/tds-algifert-k-powder.pdf"; 1 page.

(Continued)

*Primary Examiner* — Lynn Y Fan
(74) *Attorney, Agent, or Firm* — CANTOR COLBURN LLP

(57) ABSTRACT

The present invention relates to a composition of seaweed algal extracts having a dry matter content between 18-36%. These extracts preferably belong to *Ascophyllum nodosum*. The said extracts are also characterised using bioactive compounds found in them inherently. The present invention also provides a method of making the said composition and characterising the same.

18 Claims, 1 Drawing Sheet

(56)                    References Cited

OTHER PUBLICATIONS

Escanilla, R.; "Business plan for the manufacture and commercialization of a biological fertilizer based on marine algae"; University of Chile, Undergraduate Thesis; 2006; 68 pages; URI: https://repositorio.uchile.cl/handle/2250/108388; with English Abstract.

International Search Report and Written Opinion for International Application PCT/FR2015/052439; International Filing Date: Sep. 11, 2015; Date of Mailing: Dec. 2, 2015; 9 pages.

Khan, et al.; "Seaweed extracts as biostimulants of plant growth and development"; Journal of Plant Growth Regulation vol. 28, Issue No. 4; 2009; pp. 386-399.

Offei, F, et al.; "Seaweed Bioethanol Production: A Process Selection Review on Hydrolysis and Fermentation"; Fermentation, vol. 4, Issue No. 4, 99; 2018; 18 pages; DOI: https://doi.org/10.3390/fermentation4040099.

Pereira, L. et al.; "Introductory Chapter: Alginates—A General Overview"; IntechOpen; 2020; 17 pages; DOI: 10.5772/intechopen.88381.

Perez, B.; "Application of Hyperspectral Remote Sensing Techniques in Vineyard Fertilized with Extract of Seaweed"; Final Degree Project, University of Valladolid, available online at "https://docplayer.es/15470321-Universidad-de-valladolid.html"; 2004; 135 pages; with English Abstract.

Schiener, P. et al.; "The seasonal variation in the chemical composition of the kelp species Laminaria digitata, Laminaria hyperborea, Saccharina latissima and Alaria esculenta"; Journal of Applied Phycology, vol. 27; 2015; pp. 363-373; DOI: https://doi.org/10.1007/s10811-014-0327-1.

Shanmugam, H. et al.; "Algal Biotechnology: An Update From Industrial and Medical Point of View"; Omics Technologies and Bio-engineering: Towards Improving Quality of Life, Chapter 3; 2018; pp. 31-52; DOI: https://doi.org/10.1016/B978-0-12-815870-8.00003-6.

Stadnik et al.; "Algal polysaccharides as source of plant resistance inducers"; Tropical Plant Pathology, vol. 39, Issue No. 2; 2014; pp. 111-118.

Yuan, Y.; "Important Chemical Products from Magroalgae (*Ascopyllum nodosum*) Biorefinery by Assistance of Microwave Technology"; Dissertation, Doctor of Philosophy (Chemistry), University of New York; 2015; 196 pages.

Akash, et al.; Effect of different concentrations of commercial seaweed liquid extract of Ascophyllum nodosum (Organic Dews) as a plant bio stimulant on growth, yield and biochemical constituents of onion (*Allium cepa* L.): Journal of Pharmacognosy and Phytochemistry, vol. 6, Issue No. 4; 2017; pp. 658-663.

International Search Report and Written Opinion for International Application PCT/GB2020/052369; International Filing Date: Sep. 30, 2020; Date of Mailing: Jan. 12, 2021; 9 pages.

Anonymous; "Calibra: Activator of fruit and leaf equality in Summerfruit" [Datasheet]; Laboratoires Goemar SAS, New Zealand; 2014; 2 pages.

Anonymous; "Goemar Opti" [Datasheet]; Stahler from www.staehler.com; 2009; 6 pages.

Third Party Observations, EP Serial No. EP4041700, Application No. 20789656.4, dated Aug. 9, 2023.

Booth, Proc. Intl. Seaweed Symp, 6, pp. 655-662 (1969)("Booth Journal Article") (published before Dec. 31, 1969).†

TourTurf® APS Algae Plus Seaweed, Oxide:2-0-1, Product Information Overview Sheet (English), and Material Safety Data Sheet (German) (published first Aug. 22, 2015, and published as updated Sep. 18, 2017) (English translation follows).†

Third-Party Preissuance Submission Pursuant to 35 U.S.C. § 122(e) and 37 C.F.R. §1.290.†

E. Marker A/S., TourTurf® APS Algae Plus Seaweed Information.†

Booth, "The Manufacture and Properties of Liquid Seaweed Extracts," Proc. Intl. Seaweed Symp., 6, pp. 655-662 (1969).†

\* cited by examiner

† cited by third party

CONCENTRATED ALGAL EXTRACT

CROSS REFERENCE TO RELATED APPLICATIONS

This application is a National Stage application PCT/GB2020/052369, filed Sep. 30, 2020, which claims priority to European Patent Application No. 193062973.3, filed Oct. 7, 2019, both of which are incorporated by reference in their entirety herein.

FIELD OF INVENTION

The present invention relates to a concentrated algal extract having a percentage dry matter between 18.0% to 36.0% or its use to stimulate the gene expression in plants. The present invention also relates to a concentrated algal extract characterized by the presence of active agents like Fucoidans (6-12 g/kg), Glycine Betaine (8-47 mg/Kg)), Laminine (208-335 mg/Kg), and Mannitol (30-60 g/Kg).

BACKGROUND OF INVENTION

The global effect of negative climatic changes are leading to desertification, soil salination, reduced nutrients capacity of soils and like impacts that are causing dramatic effects on agricultural production and quality of crops. With increasing population and urbanization, the global amount of cultivable land is also shrinking. In order to meet the food need of fast growing population world food production needs to be doubled by 2050.

To address these issues, high productivity in agriculture is a must that can meet the rising demand of food. To achieve this, producers had started relying on the applications of chemical like synthetic fertilizers or synthetic insecticides or synthetic fungicides or like.

Plant biostimulants are input compounds or compound complexes that offer a potential alternative to traditional, agro-chemical inputs.

According to the European Biostimulants Industry Council (EBIC), "plant biostimulants contain substance(s) and/or microorganisms whose function when applied to plants or the rhizosphere is to stimulate natural processes to enhance/benefit nutrient uptake, nutrient efficiency, tolerance to abiotic stresses, and crop quality". Algae or seaweed extract are one of the input agents described as biostimulant by the EBIC.

Seaweeds are multicellular, macroscopic organisms found in coastal, marine ecosystems and possess high quantity of polysaccharides, polyunsaturated fatty acids (PUFA), enzymes, minerals, bioactive enzymes and other components. These extracts are known to enable better seed germination, especially by promoting plant emergence. The most widely researched seaweed is *Ascophyllum nodosum* and various commercial products are available from the extracts of *Ascophyllum nodosum*. These extracts have been reported to improve the plant growth.

US20170251677A1 mentions about a concentrated extract of *Ascophyllum nodosum,* and its use as biostimulant alone or in combination with other agents. The reference specifically teaches an algal extract having dry matter of 5% or 13%.

The article 'Effect of different concentrations of commercial seaweed liquid extract of *Ascophyllum nodosum* (Organic Dews) as a plant bio stimulant on growth, yield and biochemical constituents of onion (*Allium cepa* L.) by Akash et al., J. Pharmacognosy and Phytochemistry, 2017' studies the effect of different concentrations of seaweed liquid extract of *Ascophyllum nodosum* as biostimulant. The article further concludes that as the concentration of the extract is increased its impact decreases.

However, there still exists a need in the art to provide the best formulations of these extracts which are concentrated and yet effective. Since the extract of *Ascophyllum nodosum* is a complex of various biological and biochemical ingredients, its best quality and optimum use is still a pondering question. Further, the diluted extracts are meant to be applied at higher dose thus increasing the cost of farmers. Thus, there lies a need for a concentrated algal extract that has good biostimulant activity and is also cost effective.

OBJECTS OF THE INVENTION

An object of the present invention is to provide an algal extract of *Ascophyllum nodosum* having maximum efficacy.

It is an object of the present invention to provide an algal extract of *Ascophyllum nodosum* having a characteristic active agents distribution profile and the link of these markers with efficiency.

Yet another object of this invention is to provide a process for preparing an algal extract of *Ascophyllum nodosum* having a predetermined dry matter content.

Yet another object of this invention is to provide a process for preparing an algal extract of *Ascophyllum nodosum* having a characteristic active agents distribution profile leading to an improved efficacy.

Yet another object of this invention is to provide a use of seaweed extract of *Ascophyllum nodosum* for biostimulating the plant growth.

Yet another object of this invention is to provide a use of seaweed extract of *Ascophyllum nodosum* as bird repellant.

Yet another object of this invention is to provide a use of seaweed extract of *Ascophyllum nodosum* as a seed coating agent.

Yet another object of this invention is to provide a combination comprising an algal extract of *Ascophyllum nodosum* with nutritive, biostimulating or another agro-chemical.

SUMMARY OF THE INVENTION

In an aspect the present invention provides an algal extract of *Ascophyllum nodosum* with dry matter between about 18%-36%.

In an aspect the present invention provides an algal extract of *Ascophyllum nodosum* with dry matter between about 24%-36%.

In an aspect the present invention provides an algal extract of *Ascophyllum nodosum* with dry matter between about 24%-30%.

In another aspect, the present invention provides an algal extract of *Ascophyllum nodosum* characterized by the concentrations of active agents Fucoidans being about 6-15 g/kg, Glycine Betaine being about 8-47 mg/Kg, Laminine being about 208-438 mg/Kg, and Mannitol being about 30-60 g/Kg by fresh weight of the algal extract.

In another aspect, the present invention provides a process for preparation of algal extract of *Ascophyllum nodosum* with dry matter of 18%-36%.

In an aspect the present invention provides a process for preparation of algal extract of *Ascophyllum nodosum* characterized by different active agents fucoidans being about 6-12 g/kg, glycine betaine being about 8-47 mg/Kg, laminine being about 208-335 mg/Kg, and mannitol being about 30-60 g/Kg, by weight of the algal extract.

In an aspect the present invention provides the use of seaweed extract of *Ascophyllum nodosum* for biostimulating the plant growth.

In an aspect the present invention provides the use of seaweed extract of *Ascophyllum nodosum* as bird repellant.

In an aspect the present invention provides the use of seaweed extract of *Ascophyllum nodosum* as seed coating agent.

In an aspect the present invention provides the use of seaweed extract of *Ascophyllum nodosum* as animal nutrition supplement.

In an aspect the present invention provides the use of seaweed extract of *Ascophyllum nodosum* as cosmetic agent.

In an aspect the present invention provides the use of seaweed extract of *Ascophyllum nodosum* in medicines or nutraceuticals.

In an aspect the present invention provides a combination of algal extract of *Ascophyllum nodosum* with nutritive, biostimulating agent or plant-protecting composition, where the plant protecting composition is herbicide, fungicide, insecticide or pesticide.

BRIEF DESCRIPTION OF THE DRAWING

FIG. 1 shows the brix index profile of an algal extract of the present invention.

In an aspect the present invention provides a combination of algal extract of *Ascophyllum nodosum* with a super absorbent polymer.

DETAILED DESCRIPTION OF THE INVENTION

The present inventors have found that an algal extract of *Ascophyllum nodosum* that is highly concentrated and yet has all the compounds of the intracellular fluid of the alga preserved has excellent biostimulating activity. Surprisingly, the inventors have observed that, following application in very less amount of the concentrated algal extract of the invention is more effective than a diluted extract in stimulating plant emergence and promoting plant growth. It was also observed that the different components of the extract were responsible for biostimulating specific gene expressions in the plants.

Also, when the concentrated algal extract is used to coat seeds, the latter are less frequently attacked by birds than uncoated seeds.

For convenience, before further description of the present disclosure, certain terms employed in the specification, and examples are described here. These definitions should be read in the light of the remainder of the disclosure and understood as by a person of skill in the art. The terms used herein have the meanings recognized and known to those of skill in the art. However, for convenience and completeness, particular terms and their meanings are set forth below.

As used herein the term 'plant' refers to an agricultural plant having sugar content as agronomically important trait for example wheat, rye, barley, rice, triticale, oats, sorghum, sugarcane, beet, sugar beet or fodder beet, fruits like pomes, apples, pears, plums, peaches, almonds, cherries, strawberries, raspberries, blackberries or gooseberries, leguminous plants, such as lentils, peas, alfalfa or soybeans, oil plants, such as rape, oil-seed rape, canola, juncea, linseed, mustard, olives, sunflowers, coconut, cocoa beans, castor oil plants, oil palms, ground nuts or soybeans, cucurbits, such as squashes, cucumber or melons, fiber plants, such as cotton, flax, hemp or jute, citrus fruit, such as oranges, lemons, grapefruits or mandarins, vegetables, such as spinach, lettuce, asparagus, cabbages, carrots, onions, tomatoes, cucurbits or paprika, lauraceous plants, such as avocados, cinnamon or camphor, energy and raw material plants, such as corn, soybean, rape, canola, oil palm, corn, tobacco, nuts, coffee, tea, bananas, vines, hop, turf, natural rubber plants or ornamental and forestry plants, such as flowers and shrubs.

As used herein seaweed refers to the coldwater seaweed or brown alga (Phaeophyceae) of the family Fucaceae, belonging to the genus *Ascophyllum*.

Active agents are the agents that are present in the algal extract obtained by various processes of algal extraction. The algal extract may contain one or more than one active compound selected from, but not limited to polysaccharides, such as, especially, laminarin and fucans; free and conjugated sugars; polyphenols; mannitol; growth hormones; lipids; proteins; amino acids; vitamins; betaines; sterols; glucuronic acid and mineral salts.

Alternative Boron source is any Boron source that is less toxic or non-toxic than the conventional boron source. It can be selected from but not limited to Colemanite.

The term "cultivation" as used herein refers to an activity to grow plants in any stage from the seeding stage to maturation stage. It means to artificially grow plants over the entire or in partial period from the seeding stage to the maturation stage and in each following stage or in stages by the combination of two or more of the stages such as (1) from nursery stage to maturation stage; (2) from nursery plants to maturation stage; (3) from seeds to nursery plants; (4) from the stage between before the desired maturation to the desired maturation and (5) from the nursery plants to the stage before the desired maturation.

The terms "superabsorbent polymer" or "SAP" referred herein refer to the water swellable polymers which can absorb water many times their weight in an aqueous solution. Without wishing to be bound by theory, the term superabsorbent polymers also apply to polymers that absorb water as well as desorb the absorbed water. The superabsorbent polymer may be selected from but not limited to water-swellable or water absorbing or water-retentive polymers such as cross-linked polymers that swell without dissolving in the presence of water, and may, absorb at least 10, 100, 1000, or more times their weight in water.

As used herein the plant protective, nutrient and surfactant adjuvant composition is selected from but not limited to fertilizers, mycorrhiza, micronutrients, acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, virucides, derivatives thereof, biological control agents and mixtures thereof.

As used here in the gene expression describes the upregulation or downregulation of gene expression in the organism.

In an embodiment, the fertilizer is selected from organic and inorganic fertilizers such as those selected from but not limited to urea, NPK, nitrogen based fertilizers, phosphate, calcium, potassium, magnesium, sulfur, copper, iron, manganese, molybdenum, zinc, nickel, cobalt, boron and their salts and derivatives.

In an embodiment, the micronutrient is selected from but not limited to iron, manganese, boron, molybdenum, zinc, chlorine, sodium, cobalt, silicon, nickel, chlorine, aluminium, vanadium, selenium and their salts and derivatives.

Exemplary organic fertilizer may be selected from peat, limestone, rock phosphate, blood meal, bone meal, compost, humic acid, seaweed extracts, digested proteins, fish meal, feather meal, corn meal, alfalfa meal etc.

In an embodiment, the insecticide may be selected from organic or inorganic insecticide, natural or synthetic insecticide such as those selected from but not limited to: Acetylcholine esterase inhibitors (Carbamates, Triazemate, Organophosphates); GABA-gated chloride channel antagonists (Cyclodiene organochlorines, Phenylpyrazoles (Fiproles)); Nicotinic Acetylcholine receptor agonists (allosteric) (Spinosyns); Chloride channel activators (Avermectins, Milbemycins); Inhibitors of chitin biosynthesis, type 0, Lepidopteran (Benzoylureas); Inhibitors of chitin biosynthesis, type 1, Homopteran (Buprofezin); Moulting disruptor, Dipteran (Cyromazine); Ecdysone agonists/moulting disruptors (Diacylhydrazines, Azadirachtin); Octopaminergic agonists (Amitraz); Neuronal inhibitors (unknown mode of action) (Bifenazate); Aconitase inhibitors (Fluoroacetate); Synergists (P450-dependent monooxygenase inhibitors, Esterase inhibitors); Ryanodine receptor modulators (diamide); Compounds with unknown mode of action (Benzoximate, Chinomethionat, Dicofol, Pyridalyl, Borax, Tartar emetic); Compounds of unknown or non-specific mode of action (fumigants) (Alkyl halides, Chloropicrin, Sulfuryl fluoride); Sodium channel modulators (DDT, Methoxychlor, Pyrethroids, Pyrethrins); Microbial disruptors of insect midgut membranes (B.t. subsp. *Israelensis, B. sphaericus,* B.t. subsp. *Aizawai,* B.t. subsp. *kurstaki,* B.t. subsp. *tenebrionis*); Mitochondrial complex IV electron transport inhibitors (Aluminium phosphide, Cyanide, Phosphine); Mitochondrial complex III electron transport inhibitors (Coupling site II) (Hydramethylnon, Acequinocyl, Fluacrypyrim); Compounds of unknown or non-specific mode of action (Clofentezine, Hexythiazox, Etoxazole); Nicotinic Acetylcholine receptor agonists/antagonists (Neonicotinoids, Nicotine, Bensultap, Cartap hydrochloride, Nereistoxin analogues); Juvenile hormone mimics (Juvenile hormone analogues, Fenoxycarb, Pyriproxyfen); Inhibitors of oxidative phosphorylation, disruptors of ATP formation (inhibitors of ATP synthase) (Diafenthiuron, Organotin miticides, Propargite, Tetradifon); Mitochondrial complex I electron transport inhibitors (METI acaricides, Rotenone); Voltage-dependent sodium channel blockers (Indoxacarb); Inhibitors of lipid synthesis (Tetronic acid derivatives); Mitochondrial complex IV electron transport inhibitors (Aluminium phosphide, Cyanide, Phosphine); Compounds of unknown or non-specific mode of action (selective feeding blockers) (Cryolite, Pymetrozine, Flonicamid); Uncouplers of oxidative phosphorylation via disruption of proton gradient (Chlorfenapyr, DNOC).

Surprisingly, the present inventors have found that an algal extract of *Ascophyllum nodosum* that is highly concentrated and yet has all the compounds of the intracellular fluid of the alga preserved and has excellent biostimulating activity. The inventors have observed that, following application in very less amount of the concentrated algal extract of the invention is more effective than a diluted extract in stimulating plant emergence and promoting plant growth. It was also observed that the different components of the extract were responsible for biostimulating specific gene expressions in the plants.

In an embodiment the present invention provides an algal extract of *Ascophyllum nodosum* having dry matter between about 18%-36%.

In an embodiment the present invention provides an algal extract of *Ascophyllum nodosum* having dry matter between about 24%-36%.

In an embodiment the present invention provides an algal extract of *Ascophyllum nodosum* having dry matter between about 24%-36%.

In an embodiment the present invention provides an algal extract of *Ascophyllum nodosum* having dry matter between about 24%-30%.

In an embodiment the present invention provides an algal extract of *Ascophyllum nodosum* having dry matter between about 25%-29%.

In an embodiment the present invention provides an algal extract of *Ascophyllum nodosum* having dry matter between about 26%-28%.

In an embodiment the present invention provides an algal extract of *Ascophyllum nodosum* having dry matter content of about 27%.

It has been surprisingly found that an algal extract having percentage dry matter content between about 18% to 36% has surprisingly higher efficacy.

In an embodiment, the algal extract of the present invention is characterized by the concentrations of active agents Fucoidans being about 6-15 g/kg, Glycine Betaine being about 8-47 mg/Kg, Laminine being about 208-335 mg/Kg, and Mannitol being about 30-60 g/Kg by weight of the algal extract.

In an embodiment the present invention provides a process of preparation of algal extract of *Ascophyllum nodosum* with dry matter of 24%-30%.

In an embodiment the present invention provides a process of preparation of algal extract of *Ascophyllum nodosum* characterized by the concentrations of active agents Fucoidans being about 6-15 g/kg, Glycine Betaine being about 8-47 mg/Kg, Laminine being about 208-335 mg/Kg, and Mannitol being about 30-60 g/Kg by weight of the algal extract.

In an embodiment the present invention provides the use of seaweed extract of *Ascophyllum nodosum* according to the present invention for biostimulating the plant growth.

In an embodiment the present invention provides the use of seaweed extract of *Ascophyllum nodosum* according to the present invention for overexpressing the phosphorus PT2 gene, and LKT1 gene in leaves.

In an embodiment the present invention provides the use of seaweed extract of *Ascophyllum nodosum* according to the present invention for increasing the jasmonate isoleucine amount in roots.

In an embodiment the present invention provides the use of seaweed extract of *Ascophyllum nodosum* as bird repellant.

In an embodiment the present invention provides the use of seaweed extract of *Ascophyllum nodosum* as seed coating agent.

In an embodiment the present invention provides the use of seaweed extract of *Ascophyllum nodosum* as animal nutrition supplement.

In an embodiment the present invention provides the use of seaweed extract of *Ascophyllum nodosum* as cosmetic agent.

In an embodiment the present invention provides the use of seaweed extract of *Ascophyllum nodosum* in medicines or nutraceuticals.

In an embodiment the present invention provides a combination of algal extract of *Ascophyllum nodosum* with nutritive, biostimulating or plant-protecting composition or another agrochemical, where the plant protecting composition is herbicide, fungicide, insecticide or pesticide.

In an embodiment the present invention provides a combination comprising an algal extract of *Ascophyllum nodosum* having percentage dry matter content between about 18% to about 36% and at least one superabsorbent polymer.

In an embodiment the present invention provides a combination comprising an algal extract of *Ascophyllum nodosum* having percentage dry matter content between about 24% to about 30% and at least one superabsorbent polymer.

In an embodiment, the application of the algal extract of the present invention to the plants confers one or more of the following advantages: improved plant nutrient use efficiency, increased flowering, increased fruit set quality, facilitates root growth etc., which are not to be considered as limiting.

In an embodiment, the algal extract of the present invention has a pH of around 2.25-2.30.

In an embodiment, the mannitol content in the algal extract, measured between one to three months after production, is between about 4% to about 7%.

In an embodiment, the mannitol content in the algal extract, measured between one to three months after production, is between about 4.5 to 6.5%.

In an embodiment, the mannitol content in the algal extract, measured between one to three months after production, is between about 5-6%.

In an embodiment, the algal extract of the present invention is substantially free of alginate.

In an embodiment, the algal extract according to the invention may be prepared from an algal extract conventionally known from US 2017/0251677 and which includes a percentage dry matter content between 12% to 50%. This algal extract may be used as the starting material for preparing the algal extract according to the present invention.

In an embodiment, the present invention provides a process for preparing an algal extract having a dry matter content between about 18-36%.

In an embodiment, the present invention provides a process for preparing an algal extract having a dry matter content between about 24-36%.

In an embodiment, the present invention provides a process for preparing an algal extract having a dry matter content between about 24-30%.

In an embodiment, the process comprises:
(a) feeding an initial algal extract comprising dry matter between 12-50% to an evaporator heat exchanger; and
(b) passing steam through the heat exchanger to produce the algal extract of the present invention.

In an embodiment, the process comprises:
(a) feeding an initial algal extract comprising dry matter between 3-8% to an evaporator heat exchanger; and
(b) passing steam through the heat exchanger to produce the algal extract of the present invention.

In an embodiment, the steam passed through the heat exchanger is hot dry steam.

In an embodiment, steam is passed through the heat exchanger maintained at a temperature between 30-60° C.

In an embodiment, steam is passed through the heat exchanger maintained at vacuum pressure.

In an embodiment, the process comprises adding one or more preservatives to the algal extract produced in step (b) of the process.

Thus, in an embodiment, the process comprises:
(a) feeding an initial algal extract comprising dry matter between 12-50% to an evaporator heat exchanger;

(b) passing steam through the heat exchanger to produce the algal extract of the present invention; and
(c) adding one or more preservatives to the algal extract produced in step (b) of the process.

Thus, in an embodiment, the process comprises:
(a) feeding an initial algal extract comprising dry matter between 3-8% to an evaporator heat exchanger;
(b) passing steam through the heat exchanger to produce the algal extract of the present invention; and
(c) adding one or more preservatives to the algal extract produced in step (b) of the process.

In an embodiment, the process comprises decanting the algal extract produced in step (b) and removing the sediment produced therefrom to prepare the algal extract according to the present invention.

Thus, in an embodiment, the process comprises:
(a) feeding an initial algal extract comprising dry matter between 12-50% to an evaporator heat exchanger;
(b) passing steam through the heat exchanger to produce a concentrated algal extract; and
(c) decanting the algal extract produced in step (b) and removing the sediment produced therefrom to prepare the algal extract.

Thus, in an embodiment, the process comprises:
(a) feeding an initial algal extract comprising dry matter between 3-8% to an evaporator heat exchanger;
(b) passing steam through the heat exchanger to produce a concentrated algal extract; and
(d) decanting the algal extract produced in step (b) and removing the sediment produced therefrom to prepare the algal extract.

Thus, in an embodiment, the process comprises:
(a) feeding an initial algal extract comprising dry matter between 12-50% to an evaporator heat exchanger;
(b) passing steam through the heat exchanger to produce the algal extract of the present invention;
(c) adding one or more preservatives to the algal extract produced in step (b); and
(e) decanting the algal extract produced in step (c) and removing the sediment produced therefrom to prepare the algal extract.

Thus, in an embodiment, the process comprises:
(c) feeding an initial algal extract comprising dry matter between 3-8% to an evaporator heat exchanger;
(d) passing steam through the heat exchanger to produce the algal extract of the present invention;
(d) adding one or more preservatives to the algal extract produced in step (b); and
(f) decanting the algal extract produced in step (c) and removing the sediment produced therefrom to prepare the algal extract.

However, the step of sediment removal may be carried out using any other method that is conventionally known.

Thus, in an embodiment, the process comprises:
(a) feeding an initial algal extract comprising dry matter between 3-6% to an evaporator heat exchanger;
(b) passing steam through the heat exchanger to produce a concentrated algal extract; and
(c) removing sediments from the algal extract prepared in step (b) to prepare the algal extract.

Thus, in an embodiment, the process comprises:
(a) feeding an initial algal extract comprising dry matter between 12-50% to an evaporator heat exchanger;
(b) passing steam through the heat exchanger to produce the algal extract of the present invention;
(c) adding one or more preservatives to the algal extract produced in step (b); and (d) removing sediments from the algal extract prepared in step (c) to prepare the algal extract.

In an embodiment, the step of removing the sediments may be carried out by filtering the algal extract on diatomaceous earth.

In an embodiment, the step of removing the sediments may be carried out by filtering the algal extract on polymeric membranes.

In an embodiment, the polymeric membrane is polypropylene membrane.

In an embodiment, the step of removing the sediments may be carried out by centrifuging the algal extract.

In an embodiment, the step of removing the sediments may be carried out by spray drying the algal extract.

In an embodiment, the step of removing the sediments may be carried out by adding a thickener or an anti-settling agent to stabilize the sediment particles.

In an embodiment, the step of removal of sediments may be carried out by carrying out more than one of the steps of filtration on diatomaceous earth, filtration on a polymeric membrane, centrifugation, spray drying or addition of a thickener simultaneously.

In an embodiment, the present invention provides a process for preparing a composition comprising the algal extract of the invention.

The process comprises adding at least one surfactant to the algal extract of the invention prepared by any one of the processes described hereinabove.

In an embodiment, the surfactant is a wetting agent.

In an embodiment, the wetting agent has a contact angle at least greater than 80°.

In an embodiment, the process for preparing a composition comprises adding at least one sticker to the composition.

It has been found that addition of a sticker increases the rainfastness of the compositions according to the invention.

In an embodiment, the process for preparing a composition comprises adding at least one adjuvant to the composition.

It has been found that addition of an adjuvant increases the efficacy of the compositions according to the invention.

In an embodiment, the algal extract of the present invention has a brix index of at least about or greater than 5.0.

In an embodiment, the algal extract of the present invention has a brix index of at least about or greater than 15.0.

In an embodiment, the algal extract of the present invention has a brix index of at least about or greater than 25.0.

In an embodiment, the algal extract of the present invention has a brix index of at least about 35.0.

In an embodiment, the algal extract of the present invention has a brix index profile as depicted in FIG. 1.

The algal extract of the present invention may be combined with another substance to provide combinations of the invention.

Therefore, in an embodiment, the present invention provides a combination comprising:
   (a) an algal extract having a percentage dry matter content between 18-36%; and
   (b) a superabsorbent polymer.

Therefore, in an embodiment, the present invention provides a combination comprising:
   (c) an algal extract having a percentage dry matter content between 24-36%; and
   (d) a superabsorbent polymer.

Therefore, in an embodiment, the present invention provides a combination comprising:
   an algal extract having a percentage dry matter content between 24-30%; and
   a superabsorbent polymer.

The choice of the particular superabsorbent polymer is not particularly limiting. Any superabsorbent polymer may be used.

In an embodiment, the superabsorbent polymer is selected from the group consisting of copolymer of acrylamide and sodium acrylate; hydrolyzed starch-polyacrylonitrile; 2-propenenitrile homopolymer, hydrolyzed, sodium salt or poly (acrylamide co-sodium acrylate) or poly(2-propenamide-co-2-propanoic acid, sodium salt); starch-g-poly (2propenamide-co-2-propanoic acid, mixed sodium and aluminum salts); starch-g-poly(2-propenamide-co-2-propanoic acid, potassium salt); poly(2-propenamide-co-2-propanoic acid, sodium salt); poly-2-propanoic acid, sodium salt; starch-gpoly(acrylonitrile) or poly(2-propenamide-co-sodium acrylate); starch/acrylonitrile copolymer; crosslinked copolymers of acrylamide and sodium acrylate; acrylamide/sodium polyacrylate crosslinked polymers; anionic poly acrylamide; starch grafted sodium polyacrylates; acrylic acid polymers, sodium salt; crosslinked potassium polyacrylate/polyacrylamide copolymers; sodium polyacrylate; superabsorbent polymer laminates and composites; pectins; partial sodium salt of crosslinked polypropenoic acid; potassium polyacrylate, lightly crosslinked; sodium polyacrylate, lightly crosslinked; sodium polyacrylates; poly (sodiumacrylate) homopolymer; polyacrylamide polymers, carrageenan, agar, alginic acid, guar gums and its derivatives, and gellan gum; Specific superabsorbent polymers include crosslinked copolymer of acrylamide and potassium acrylate.

In another embodiment, the algal extract of the invention may be combined with at least another agrochemical.

Therefore, in an embodiment, the present invention provides a combination comprising:
   (a) an algal extract having a percentage dry matter content between 18-36%; and
   (b) at least another agrochemical selected from fertilizers, mycorrhiza, micronutrients, acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, virucides, derivatives thereof, biological control agents and mixtures thereof.

Therefore, in an embodiment, the present invention provides a combination comprising:
   (c) an algal extract having a percentage dry matter content between 24-36%; and
   (d) at least another agrochemical selected from fertilizers, mycorrhiza, micronutrients, acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, virucides, derivatives thereof, biological control agents and mixtures thereof.

Therefore, in an embodiment, the present invention provides a combination comprising:
   (a) an algal extract having a percentage dry matter content between 24-30%; and
   (b) at least another agrochemical selected from fertilizers, mycorrhiza, micronutrients, acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, virucides, derivatives thereof, biological control agents and mixtures thereof.

In an embodiment, the fertilizer may be selected from organic and inorganic fertilizers such as those selected from but not limited to urea, NPK, nitrogen based fertilizers, phosphate, calcium, potassium, magnesium, sulfur, copper, iron, manganese, molybdenum, zinc, nickel, cobalt, boron and their salts and derivatives. Exemplary organic fertilizer may be selected from peat, limestone, rock phosphate, blood meal, bone meal, compost, humic acid, seaweed extracts, digested proteins, fish meal, feather meal, corn meal, alfalfa meal etc.

In a preferred embodiment, the fertilizer may be an inorganic fertilizer selected from NPK, derivatives of potassium, zinc, phosphate such as those selected from but not limited to potassium fertilizers such as potassium carbonate, potassium chloride (also known as muriate of potash), potassium sulfate, potassium nitrate, sulfate of potash magnesia; zinc fertilizers such as those selected from zinc sulfate, zinc oxide, zinc ammonia complex; phosphate fertilizer such as Di-ammonium phosphate, Monoammonium phosphate, Ammonium polyphosphate, Triple superphosphate or mixtures thereof. In an embodiment, the fertilizer may be an organic fertilizer selected from urea, rock potash seaweed extract, compost, humic acid, alfalfa meal, corn meal, and mixtures thereof. In an embodiment, the present invention may provide a composition comprising at least one superabsorbent polymer, at least one water soluble phosphate and a fertilizer mix of organic and inorganic fertilizers.

In an embodiment, the second agrochemical may be a biological control agent.

In a preferred embodiment, the biological control agent may be selected from complete organism or extracts of bacteria or fungi or algae or yeast or combinations thereof.

The composition combines with a micro-biological entity such as bacteria, fungi that is used in isolation or combined with other strains. The strains of bacteria that may be used for the composition include but are not limited to: *Pseudomonas* spp., *Bacillus* spp., *Sinorhizobium* spp., *Azotobacter* spp., *Beijerinkia* spp., *Clostridium* spp., *Azollae* spp., *Nitrosomonas* spp., *Nitrobacter* spp., *Tsukamorella* spp., *Nostoc* spp., *Enterobacter* spp., *Thiobacillus* spp., *Microspora* spp., *Beggiato* spp., *Paracoccus* spp., Purple Sulphur Bacteria, Green Sulphur Bacteria, *Acidanus* spp., *Sulpholobus*, *Microbacterium* spp., *Frateuria* spp., *Azospirillus* spp., *Frankia* spp., *Azospirillium* spp., *Anabaena* spp., *Azollae* spp., *Brevibacillus* spp., *Fusarium* spp., *Rhizoctonia* spp., *Pythium* spp., *Lactobacillus*, *Ensifer* spp., *Trichodesmium* spp., *Spirillium* spp., *Klebsiella* spp., *Mesorhizobium* spp., *Azorhizobium* spp., *Acidothiobacillus* spp., *Paenibacillus* spp., *Burkholderia* spp., *Alcaligenesa-cinetobacter* spp., *Arthrobacter* spp., *Erwinia* spp., *Flavobacterium* spp., *Serratia* spp., *Herbaspirrilum* spp., *Achromobacter* spp., *Aeromonus* spp., *Phyllobacterium* spp., *Micrococcus* spp., *Rhodococcus* spp., and combinations thereof.

The strains of fungi that may be used for the composition include but are not limited to.*Pantoea* spp., *Penicillium* spp., *Aspergillus* spp., *Glomus* spp., *Gigaspora* spp., *Acaulospora* spp., *Scutellospora* spp., *Trichoderma* spp., *Beauveria* spp., *Mychorizza* spp., *Chaetomium* spp., *Gliocladium* spp., *Pisolithus* spp., *Amanita* spp., *Cantharellus* spp., *Pythium* spp., and combination thereof.

In an embodiment, the algal extract of the invention may be combined with a second insecticide, fungicide or a herbicide, the choice of which is not particularly limiting.

In an embodiment, the algal extract of the present invention may be provided as a stable formulation/composition. In this embodiment, the algal extract may be coformulated with a preservative, the choice of which is not limiting.

Thus, in an embodiment, the present invention provides a composition comprising:
 (a) an algal extract having a percentage dry matter content between 18-36%; and
 (b) a preservative.

Thus, in an embodiment, the present invention provides a composition comprising:
 (c) an algal extract having a percentage dry matter content between 24-36%; and
 (d) a preservative.

Thus, in an embodiment, the present invention provides a composition comprising:
 (a) an algal extract having a percentage dry matter content between 24-30%; and
 (b) a preservative.

In an embodiment, the preservative may be selected from one or more of citric acid monohydrate, sodium methylparaben, potassium sorbate, or sodium metabisulfite.

Thus, in an embodiment, the present invention provides a composition comprising:
 (a) an algal extract having a percentage dry matter content between 18-36%; and
 (b) one or more of a preservative selected from citric acid monohydrate, sodium methylparaben, potassium sorbate, or sodium metabisulfite.

Thus, in an embodiment, the present invention provides a composition comprising:
 (c) an algal extract having a percentage dry matter content between 24-36%; and
 (d) one or more of a preservative selected from citric acid monohydrate, sodium methylparaben, potassium sorbate, or sodium metabisulfite.

Thus, in an embodiment, the present invention provides a composition comprising:
 (e) an algal extract having a percentage dry matter content between 24-30%; and
 (f) one or more of a preservative selected from citric acid monohydrate, sodium methylparaben, potassium sorbate, or sodium metabisulfite.

In an embodiment, the present invention provides a combination comprising:
 (a) an algal extract having a percentage dry matter content between 24-30% in an amount greater than 90% by weight of the composition; and
 (b) a preservative in an amount less than 10% by weight of the composition, wherein the preservative is selected from citric acid monohydrate, sodium methylparaben, potassium sorbate, or sodium metabisulfite.

In an embodiment, the present invention provides a combination comprising:
 (a) an algal extract having a percentage dry matter content between 24-30% in an amount of about 99.5% by weight of the composition; and
 (b) citric acid monohydrate in an amount of about 0.5% by weight of the composition.

In an embodiment, the present invention provides a combination comprising:
 (a) an algal extract having a percentage dry matter content between 18-36% in an amount of about 99.6% by weight of the composition;

(b) sodium methylparaben in an amount of about 0.1% by weight of the composition;

(c) potassium sorbate in an amount of about 0.1% by weight of the composition; and (d) sodium metabisulfite in an amount of about 0.2% by weight of the composition.

In an embodiment, the present invention provides a combination comprising:

(e) an algal extract having a percentage dry matter content between 24-36% in an amount of about 99.6% by weight of the composition;

(f) sodium methylparaben in an amount of about 0.1% by weight of the composition;

(g) potassium sorbate in an amount of about 0.1% by weight of the composition; and (h) sodium metabisulfite in an amount of about 0.2% by weight of the composition.

In an embodiment, the present invention provides a combination comprising:

(a) an algal extract having a percentage dry matter content between 24-30% in an amount of about 96.6% by weight of the composition;

(b) citric acid in an amount of about 3.0% by weight of the composition;

(c) sodium methylparaben in an amount of about 0.1% by weight of the composition; and (d) sodium metabisulfite in an amount of about 0.2% by weight of the composition.

In an embodiment, the algal extract of the present invention comprises mineral matter in an amount of about 20%-45% by weight of the extract.

In an embodiment, the algal extract of the present invention comprises mineral matter in an amount of about 22%-41% by weight of the extract.

In an embodiment, the algal extract of the present invention comprises mineral matter in an amount of about 31.5% by weight of the extract.

In an embodiment, the algal extract of the present invention comprises polyphenols in an amount of about 5%-20% by weight of the extract.

In an embodiment, the algal extract of the present invention comprises polyphenols in an amount of about 8%-19% by weight of the extract.

In an embodiment, the algal extract of the present invention comprises polyphenols in an amount of about 13.5% by weight of the extract.

In an embodiment, the algal extract of the present invention comprises proteins in an amount of about 1%-6% by weight of the extract.

In an embodiment, the algal extract of the present invention comprises proteins in an amount of about 3.5% by weight of the extract.

In an embodiment, the algal extract of the present invention comprises mannitol in an amount of about 4%-23% by weight of the extract.

In an embodiment, the algal extract of the present invention comprises mannitol in an amount of about 13.5% by weight of the extract.

In an embodiment, the algal extract of the present invention comprises fucoidans in an amount of about 1%-6% by weight of the extract.

In an embodiment, the algal extract of the present invention comprises fucoidans in an amount of about 3.5% by weight of the extract.

In an embodiment, the algal extract of the present invention comprises glucose in an amount of about 3%-13% by weight of the extract.

In an embodiment, the algal extract of the present invention comprises glucose in an amount of about 8.0% by weight of the extract.

The term substantially free of an alginate means that the algal extract of the present invention comprises less than 0.1% of alginic acid by weight of the extract. Preferably, less than 0.05% of alginic acid is present.

The advantages offered by the present invention will be more apparent from the examples set forth herein below. These examples are provided merely as illustrations of the invention and are not intended to be construed as a limitation thereof.

EXAMPLES

The following examples are meant to illustrate the present invention. The examples are presented to exemplify the invention and are not to be considered as limiting the scope of the present invention.

Seaweed extract was harvested from North East Atlantic Ocean. The extracted seaweed was subjected to crushing and micro-crushing. To the crushed seaweed 0.5% citric acid was added. The mixture was subjected to flocculation under acidic conditions, and filtered via filter press. The filtrate was concentrated through vacuum evaporation to prepare an extract having 24-30% dry matter content.

To the concentrated algal extract was added sodium methyl paraben (0.1%), potassium sorbate (0.1%) and sodium metabisulfite (0.2%). The composition was centrifuged for removal of sediment and filtered on diatomaceous earth.

Comparative algal extracts were produced according to Example 1 (5.1%) and Example 2 (13.00%) of US 2017/0251677. A slight variation was seen in the dry matter content as the actual percentage dry matter content was measured to be 4.8% and 9.3% versus 5.1% and 13.0% respectively.

The three algal extracts were then subjected to efficacy tests, and approximate equivalent bio-activity rate in oz/acre for the three algal extracts were noted.

| | % Dry Matter | | Avg % Dry Matter | Approximate Equivalent Bio Activity Rate (oz/Acre) | Relative efficacy (Calculated) |
|---|---|---|---|---|---|
| Example 2 | 8.5% | 10.0% | 9.3% | 32 | 1 |
| Example 1 | 4.0% | 5.5% | 4.8% | 8 | 4 |
| Algal extract of the present invention | 24.0% | 30.0% | 27.0% | 1 | 32 |

It was thus surprisingly found that the algal extract of the present invention was 32 times more efficacious than example 2, and 8 times more efficacious than example 1 of US 2017/0251677. Thus, the selection of percentage dry matter content between 24 to 36%, and specifically about 27.0%, conferred unexpected and surprising efficacy on the algal extract of the present invention.

We claim:

1. A seaweed algal extract comprising a percent dry matter between about 18%-36% by weight, wherein, relative to fresh weight, the algal extract has: fucoidans at 6-15 g per kg; glycine betaine at 8-47 mg per kg; laminine at 208-438 mg per kg; and mannitol at 30-60 g per kg.

2. The extract as claimed in claim 1, wherein the seaweed is a coldwater seaweed or brown alga of the family Phaeophyceae.

3. The extract as claimed in claim 1, wherein the seaweed belongs to family Fucaceae.

4. The extract as claimed in claim 3, the said seaweed is *Ascophyllum nodosum*.

5. A process for preparation of an algal extract, said process consisting of:
   a. feeding an initial algal extract comprising dry matter between 3-8% by weight to an evaporator heat exchanger;
   b. passing steam through the heat exchanger, transferring heat to the initial algal extract, generating in the heat exchanger an algal extract according to claim 1 and sediment; and
   c. decanting from the heat exchanger the algal extract produced in step b and removing sediment produced therefrom to produce the algal extract having a percent dry matter between about 18%-36% by weight and less than 1% alginic acid.

6. The process as claimed in claim 5, wherein said process further comprises adding one or more preservatives to the algal extract produced in step (b) of the process.

7. A method of biostimulating plant physiology comprising applying to a plant the extract of claim 1.

8. A composition comprising an algal extract of *Ascophyllum nodosum* having a percent dry matter between about 18%-36% by weight and a biostimulating agent or plant-protecting composition, where the plant protecting composition comprises an herbicide, fungicide, insecticide or pesticide, and, wherein, relative to fresh weight, the algal extract has: fucoidans at 6-15 g per kg; glycine betaine at 8-47 mg per kg; laminine at 208-438 mg per kg; and mannitol at 30-60 g per kg.

9. The composition of claim 8, wherein the biostimulating agent is a fertilizer or micronutrient.

10. A composition comprising an algal extract of *Ascophyllum nodosum* having a percent dry matter between about 18%-36% and a super absorbent polymer, wherein, relative to fresh weight, the algal extract has: fucoidans at 6-15 g per kg; glycine betaine at 8-47 mg per kg; laminine at 208-438 mg per kg; and mannitol at 30-60 g per kg.

11. The extract as claimed in claim 4 having a percent dry matter between about 24%-30% by weight.

12. The extract as claimed in claim 4 having a percent dry matter between about 25%-29% by weight.

13. The extract as claimed in claim 4 having a percent dry matter between about 26%-28% by weight.

14. The extract as claimed in claim 4 having a percent dry matter content of about 27% by weight.

15. The process as claimed in claim 5, wherein the initial algal extract comprises dry matter between 3-6% by weight.

16. The process as claimed in claim 6, wherein the one or more preservatives are selected from a group consisting of citric acid monohydrate, sodium methylparaben, potassium sorbate and sodium metabisulfite.

17. The process as claimed in claim 5, wherein the removal of the sediment is carried out by one or more of filtration or diatomaceous earth, filtration on a polymeric membrane, centrifugation, spray drying or addition of a thickener or an anti-settling agent.

18. A process for preparation of an algal extract, said process consisting of:
   a. feeding an initial algal extract comprising dry matter between 3-8% by weight to an evaporator heat exchanger;
   b. passing steam through the heat exchanger, transferring heat to the initial algal extract, generating in the heat exchanger an algal extract and sediment; and
   c. decanting from the heat exchanger the algal extract produced in step b and removing sediment produced therefrom to produce the algal extract; and, wherein the algal extract has a percent dry matter between about 18%-36% by weight;
   wherein the algal extract has less than 1% alginic acid;
   wherein, relative to fresh weight, the algal extract has: fucoidans at 6-15 g per kg;
   glycine betaine at 8-47 mg per kg; laminine at 208-438 mg per kg; and mannitol at 30-60 g per kg.

* * * * *